US010758147B2

(12) United States Patent
Relan et al.

(10) Patent No.: US 10,758,147 B2
(45) Date of Patent: Sep. 1, 2020

(54) METHODS AND SYSTEMS FOR MAPPING CARDIAC ACTIVITY

(71) Applicant: St. Jude Medical, Cardiology Division, Inc., St. Paul, MN (US)

(72) Inventors: Jatin S. Relan, Bordeaux (FR); Valtino X. Afonso, Oakdale, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 38 days.

(21) Appl. No.: 16/073,857

(22) PCT Filed: Feb. 21, 2017

(86) PCT No.: PCT/US2017/018659
§ 371 (c)(1),
(2) Date: Jul. 30, 2018

(87) PCT Pub. No.: WO2017/151347
PCT Pub. Date: Sep. 8, 2017

(65) Prior Publication Data
US 2019/0038165 A1    Feb. 7, 2019

Related U.S. Application Data

(60) Provisional application No. 62/301,866, filed on Mar. 1, 2016.

(51) Int. Cl.
*A61B 5/0468*    (2006.01)
*A61B 5/00*    (2006.01)
(Continued)

(52) U.S. Cl.
CPC ............ *A61B 5/0468* (2013.01); *A61B 5/044* (2013.01); *A61B 5/0452* (2013.01);
(Continued)

(58) Field of Classification Search
CPC ...... A61B 5/0468; A61B 5/0452; A61B 5/726
See application file for complete search history.

(56) References Cited

U.S. PATENT DOCUMENTS 5,697,377 A    12/1997    Wittkampf
5,983,126 A    11/1999    Wittkampf
(Continued)

FOREIGN PATENT DOCUMENTS

JP    2012-508079    4/2012
JP    2012-524614    10/2012
(Continued)

OTHER PUBLICATIONS

International Search Report and Written Opinion for PCT/US2017/018659, dated Apr. 5, 2017.

*Primary Examiner* — George R Evanisko
(74) *Attorney, Agent, or Firm* — Wiley Rein LLP

(57) ABSTRACT

Cardiac activity can be mapped by receiving an electrogram, transforming the electrogram into the wavelet domain (e.g., using a continuous wavelet transformation) to create a scalogram of the electrogram, computing at least one energy function of the scalogram, and computing at least one metric of the electrogram using the at least one energy function. The metrics of the electrogram can include, without limitation: a QRS activity duration for the electrogram; a near-field component duration for the electrogram; a far-field component duration for the electrogram; a number of multiple components for the electrogram; a slope of a sharpest component of the electrogram; a scalogram width; an energy ratio in the electrogram; and a cycle-length based metric of the electrogram.

17 Claims, 10 Drawing Sheets

(51) Int. Cl.
*A61B 5/0452* (2006.01)
*A61B 5/044* (2006.01)
*A61B 5/0456* (2006.01)

(52) U.S. Cl.
CPC .......... *A61B 5/0456* (2013.01); *A61B 5/7203* (2013.01); *A61B 5/726* (2013.01); *A61B 5/7221* (2013.01); *A61B 5/7239* (2013.01); *A61B 5/7264* (2013.01)

(56) References Cited

U.S. PATENT DOCUMENTS

| | | | |
|---|---|---|---|
| 6,640,119 | B1 | 10/2003 | Budd et al. |
| 6,728,562 | B1 | 4/2004 | Budd et al. |
| 6,939,309 | B1 | 9/2005 | Beatty et al. |
| 6,947,785 | B1 | 9/2005 | Beatty et al. |
| 6,978,168 | B2 | 12/2005 | Beatty et al. |
| 6,990,370 | B1 | 1/2006 | Beatty et al. |
| 7,263,397 | B2 | 8/2007 | Hauck et al. |
| 7,885,707 | B2 | 2/2011 | Hauck |
| 2007/0129639 | A1* | 6/2007 | Zhang .................. A61B 5/0452 600/509 |
| 2010/0274148 | A1 | 10/2010 | Zhang et al. |
| 2011/0077538 | A1 | 3/2011 | Liu et al. |
| 2012/0289846 | A1 | 11/2012 | Zhang et al. |
| 2015/0272464 | A1 | 10/2015 | Armoundas |
| 2016/0022164 | A1 | 1/2016 | Brockway et al. |

FOREIGN PATENT DOCUMENTS

| | | |
|---|---|---|
| JP | 2015-139707 | 8/2015 |
| JP | 2015-530160 | 10/2015 |
| WO | 20150164833 | 10/2015 |

* cited by examiner

METHODS AND SYSTEMS FOR MAPPING CARDIAC ACTIVITY

CROSS-REFERENCE TO RELATED APPLICATIONS

This application claims the benefit of U.S. provisional application No. 62/301,866, filed 1 Mar. 2016, which is hereby incorporated by reference as though fully set forth herein.

BACKGROUND

The instant disclosure relates to electrophysiological mapping, such as may be performed in cardiac diagnostic and therapeutic procedures. In particular, the instant disclosure relates to systems, apparatuses, and methods for mapping multi-component cardiac activity.

While mapping within and around scar or wall thinning, such as in subjects with Ischemic or Dilated Cardiomyopathy, sharp fractionated bi-polar potentials representing the local near-field activity can appear to be fused with the far-field electrogram. These sharp potentials often take one of two morphology forms. In Form 1, the near-field potentials are separated from the far-field potentials by an isoelectric line and extend beyond the QRS end of a surface ECG. In Form 2, the near-field potentials appear fused with the far-field potential and buried within the QRS activity of the surface ECG.

It would be desirable to be able to detect such multi-component signals and to decouple the various components thereof.

BRIEF SUMMARY

Disclosed herein is a method of mapping cardiac activity, including: receiving an electrogram signal S(t) at a signal processor; and using the signal processor: transforming the electrogram signal S(t) into the wavelet domain, thereby computing a scalogram. G(f, t); computing at least one energy function. L(t) of the scalogram G(f, t); and computing at least one metric of the electrogram signal S(t) using the at least one energy function. L(t). The electrogram signal S(t) can be transformed into the wavelet domain by applying a continuous wavelet transformation to the electrogram signal S(t) to compute the scalogram G(f, t). Further, values of G(f, t) less than a preset noise threshold can be set to zero. The method can also include generating a graphical representation of the at least one metric of the electrogram signal S(t) on a cardiac model.

In embodiments, the at least one energy function L(t) is of form $L(t)=\Sigma G(f,t)$, where f can be between 0 Hz and 1000 Hz. According to other aspects of the disclosure, f can be within a cardiac activity frequency range defined by a preset lower frequency limit and a preset upper frequency limit.

It is contemplated that the step of computing at least one metric of the electrograin signal S(t) using the at least one energy function L(t) can include computing a QRS activity duration for the electrogram signal S(t), such as by: computing a pulse wave $L^{Pulse}(t)$ having a pulse duration according to an equation $$L^{Pulse}(t) = \begin{cases} 1, \text{ if } L(t) > 0 \\ 0, \text{ otherwise} \end{cases};$$

and defining the QRS activity duration for the electrogram signal S(t) to be equal to the pulse duration.

The method can also include: detecting a plurality of local maximum peaks in the at least one energy function L(t); and categorizing each local maximum peak of the plurality of local maximum peaks as a near-field peak, a far-field peak, or a noise peak. For example, a local maximum peak can be categorized a near-field peak if the at least one energy function L(t) exceeds a preset near field threshold at the local maximum peak; as a far-field peak if the at least one energy function L(t) exceeds a preset far field threshold and not the preset near field threshold at the local maximum peak; and as a noise peak otherwise.

In other embodiments disclosed herein, the step of computing at least one metric of the electrogram signal S(t) using the at least one energy function L(t) includes computing at least one of a near-field component duration and a far-field component duration for the electrogram signal S(t) by a method including the following steps: computing a pulse wave $L^{Pulse}(t)$ having one or more pulses according to an equation $$L^{Pulse}(t) = \begin{cases} 1, \text{ if } L(t) > 0 \\ 0, \text{ otherwise} \end{cases};$$

and for each pulse of the one or more pulses of the pulse wave $L^{Pulse}(t)$: if the pulse includes a near-field peak, defining the near-field component duration for the electrogram signal S(t) to be equal to a duration of the pulse; and if the pulse includes a far-field peak, defining the far-field component duration for the electrogram signal S(t) to be equal to the duration of the pulse.

In still further embodiments, the step of computing at least one metric of the electrogram signal S(t) using the at least one energy function L(t) can include computing a number of multiple components for the electrogram signal S(t), wherein the number of multiple components for the electrogram signal S(t) is defined to be equal to a total number of the plurality of local maximum peaks in the at least one energy function L(t).

In yet further embodiments of the disclosure, the step of computing at least one metric of the electrogram signal S(t) using the at least one energy function L(t) can include computing a slope of a sharpest component of the electrogram S(t). This can be accomplished, for example, by: identifying a maximum energy near-field peak of the plurality of local maximum peaks in the at least one energy function L(t); computing a maximum value of a first derivative S'(t) of the electrogram signal S(t) within a preset refractory window surrounding the maximum energy near-field peak; and defining the maximum value of the first derivative S'(t) of the electrogram signal S(t) within the preset refractory window as the slope of the sharpest component of the electrogram signal S(t). Alternatively, a scalogram width can be used to determine the slope of the sharpest component.

In still further embodiments disclosed herein, the step of computing at least one energy function L(t) of form $L(t)=\Sigma G(f,t)$ includes: computing a high frequency energy function $L^{High}(t)=\Sigma G(f^{High},t)$; and computing a low frequency energy function $L^{Low}(t)=\Sigma G(f^{Low},t)$; and computing at least one metric of the electrogram signal S(t) using the at least one energy function L(t) includes computing a ratio of $L^{High}(t)$ to $L^{Low}(t)$. $f^{High}$ can be between 60 Hz and 300 Hz and $f^{Low}$ can be between 10 Hz and 60 Hz.

It is also contemplated that the step of computing at least one metric of the electrogram signal S(t) using the at least one energy function L(t) can include computing a cycle-length based metric using the ratio of $L^{High}(t)$ to $L^{Low}(t)$. For example, computing the cycle-length based metric using the ratio of $L^{High}(t)$ to $L^{Low}(t)$ can include computing the cycle-length based metric based upon a plurality of local activation times detected when the ratio of $L^{High}(t)$ to $L^{Low}(t)$ exceeds a preset threshold.

Also disclosed herein is a system for mapping cardiac activity, including: a wavelet transformation processor configured: to receive an electrogram S(t); to transform the electrogram signal S(t) into the wavelet domain, thereby computing a scalogram G(f,t); and to compute at least one energy function L(t) of the scalogram G(f,t); and a mapping processor configured to compute at least one metric of the electrogram signal S(t) in the wavelet domain using the at least one energy function L(t). The mapping processor can be further configured to output a graphical representation of the at least one metric of the electrogram signal S(t) on a cardiac model. The at least one metric of the electrogram signal S(t) can be selected from the group consisting of: a QRS activity duration for the electrogram signal S(t); a near-field component duration for the electrogram signal S(t); a far-field component duration for the electrogram signal S(t); a number of multiple components for the electrogram signal S(t); a slope of a sharpest component of the electrogram signal S(t); a scalogram width; an energy ratio in the electrogram signal S(t); and a cycle-length based metric of the electrogram signal S(t).

The foregoing and other aspects, features, details, utilities, and advantages of the present invention will be apparent from reading the following description and claims, and from reviewing the accompanying drawings.

DETAILED DESCRIPTION

The present disclosure provides methods, apparatuses, and systems for the creation of electrophysiology maps (e.g., electrocardiographic maps) that provide information regarding cardiac activity. Certain embodiments of the disclosure will be explained with reference to the use of bipolar electrograms to create electrophysiology maps of wavelet domain metrics. It should be understood, however, that the teachings herein can be applied in other contexts where it is desirable to discern a localized phenomenon from a far-field phenomenon. For example, the teachings herein can be applied to differentiate fetal cardiac signals from maternal cardiac signals or to differentiate localized brain activity from more distant brain activity in an electroencephalogram ("EEG").

Figure 1:
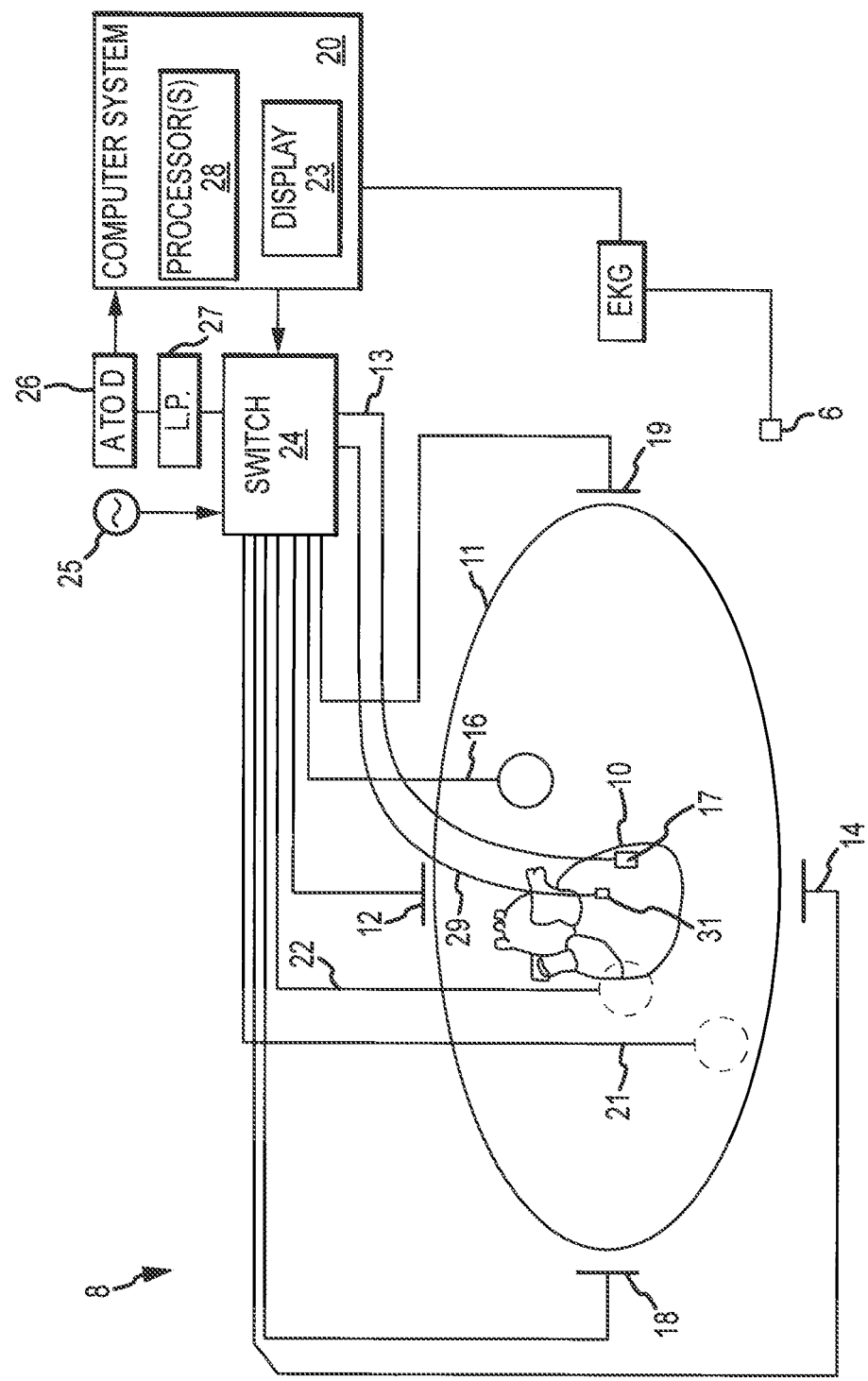
FIG. 1 is a schematic of an electrophysiology system, such as may be used in an electrophysiology study including mapping cardiac repolarization activity.

FIG. 1 shows a schematic diagram of an electrophysiology system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data, including, but not limited to, electrical activation data (e.g., local activation time ("LAT")), at a plurality of points along a cardiac surface and store the measured data in association with location information for each measurement point at which the electrophysiology data was measured, for example to create an electrophysiology map of the patient's heart 10 (or a portion thereof).

As one of ordinary skill in the art will recognize, and as will be further described below, system 8 can determine the location, and in some aspects the orientation, of objects, typically within a three-dimensional space, and express those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body or on an external frame.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only one lead 6 and its connection to computer system 20 is illustrated in FIG. 1.

A representative catheter 13 having at least one electrode 17 (e.g., a distal electrode) is also depicted in schematic fashion in FIG. 1. This representative catheter electrode 17 can be referred to as a "measurement electrode" or a "roving electrode." Typically, multiple electrodes on catheter 13, or on multiple such catheters, will be used. In one embodiment, for example, system 8 may utilize sixty-four electrodes on twelve catheters disposed within the heart and/or vasculature of the patient.

In other embodiments, system 8 may utilize a single catheter that includes multiple (e.g., eight) splines, each of which in turn includes multiple (e.g., eight) electrodes. Of course, these embodiments are merely exemplary, and any number of electrodes and catheters may be used. Indeed, in some embodiments, a high density mapping catheter, such as the EnSite™ Array™ non-contact mapping catheter of St. Jude Medical, Inc., can be utilized.

Figure 2:
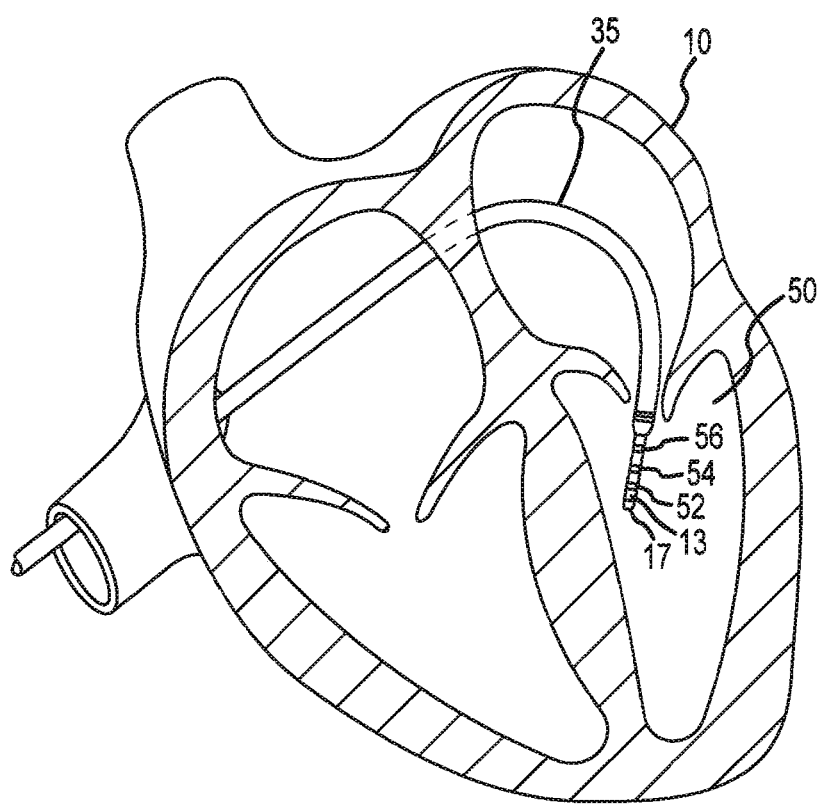
FIG. 2 depicts an exemplary multi-electrode catheter used in an electrophysiology study.

Likewise, it should be understood that catheter 13 (or multiple such catheters) are typically introduced into the heart and/or vasculature of the patient via one or more introducers and using familiar procedures. For purposes of this disclosure, a segment of an exemplary multi-electrode catheter 13 is shown in FIG. 2. In FIG. 2, catheter 13 extends into the left ventricle 50 of the patient's heart 10 through a transseptal sheath 35. The use of a transseptal approach to the left ventricle is well known and will be familiar to those of ordinary skill in the art, and need not be further described herein. Of course, catheter 13 can also be introduced into the heart 10 in any other suitable manner.

Catheter 13 includes electrode 17 on its distal tip, as well as a plurality of additional measurement electrodes 52, 54, 56 spaced along its length in the illustrated embodiment. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by system 8.

Similarly, each of electrodes 17, 52, 54, and 56 can be used to gather electrophysiological data from the cardiac surface. The ordinarily skilled artisan will be familiar with various modalities for the acquisition and processing of electrophysiology data points (including, for example, both contact and non-contact electrophysiological mapping and the collection of both unipolar and bipolar electrograms), such that further discussion thereof is not necessary to the understanding of the cardiac repolarization activity mapping techniques disclosed herein. Likewise, various techniques familiar in the art can be used to generate a graphical representation from the plurality of electrophysiology data points. In so far as the ordinarily skilled artisan will appreciate how to create electrophysiology maps from electrophysiology data points, the aspects thereof will only be described herein to the extent necessary to understand the maps disclosed herein.

Returning now to FIG. 1, in some embodiments, a fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20, for example, may comprise a conventional general-purpose computer, a special-purpose computer, a distributed computer, or any other type of computer. The computer 20 may comprise one or more processors 28, such as a single central processing unit (CPU), or a plurality of processing units, commonly referred to as a parallel processing environment, which may execute instructions to practice the various aspects disclosed herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any other number of electrodes) could be positioned in any other effective arrangement for driving a current to or sensing a current from an electrode in the heart. For example, multiple electrodes could be placed on the back, sides, and/or belly of patient 11. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17, 52, 54, 56 placed in the heart 10 are exposed to the field from a current pulse and are measured with respect to ground, such as belly patch 21. In practice the catheters within the heart 10 may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which localization system 8 measures positions. Data sets from each of the surface electrodes, the internal electrodes, and the virtual electrodes may all be used to determine the location of the roving electrodes 17, 52, 54, 56 within heart 10.

The measured voltages may be used by system 8 to determine the location in three-dimensional space of the electrodes inside the heart, such as roving electrodes 17, 52, 54, 56, relative to a reference location, such as reference electrode 31. That is, the voltages measured at reference electrode 31 may be used to define the origin of a coordinate system, while the voltages measured at roving electrodes 17, 52, 54, 56 may be used to express the location of roving electrodes 17, 52, 54, 56 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

In one representative embodiment, the system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ cardiac mapping and visualization system of St. Jude Medical, Inc., which generates electrical fields as described above, or another localization system that relies upon electrical fields. Other localization systems, however, may be used in connection with the present teachings, including for example, systems that utilize magnetic fields instead of or in addition to electrical fields for localization. Examples of such systems include, without limitation, the CARTO navigation and location system of Biosense Webster, Inc., the AURORA® system of Northern Digital Inc., Sterotaxis' NIOBE® Magnetic Navigation. System, as well as MediGuide™ Technology and the EnSite Precision™ system, both from St. Jude Medical, Inc.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

One basic methodology of mapping cardiac activity will be explained with reference to the flowchart 300 of representative steps presented as FIG. 3. In some embodiments, for example, flowchart 300 may represent several exemplary steps that can be carried out by the computer 20 of FIG. 1 (e.g., by one or more processors 28 executing one or more specialized modules, such as a wavelet transformation processor executing a wavelet transformation module as further described below) to generate a map of cardiac activity as described herein. It should be understood that the representative steps described below can be hardware-implemented, software-implemented, or both. For the sake of explanation, the term "signal processor" is used herein to describe both hardware- and software-based implementations of the teachings herein. Likewise, it should be understood that the teachings herein can be executed on a single CPU, which may have one or more threads, or distributed across multiple CPUs, each of which may have one or more threads, in a parallel processing environment.

In step 302, an electrogram signal, denoted S(t) (and illustrated as trace 402 in panel A of FIG. 4), is received at a signal processor (e.g., by one or more processors 28 within computer 20). According to aspects of the disclosure, the electrogram signal S(t) is a bipolar signal. It is contemplated, however, that the teachings herein can also be applied to unipolar electrogram signals and/or to monophasic action potential ("MAP") signals.

Figure 4:
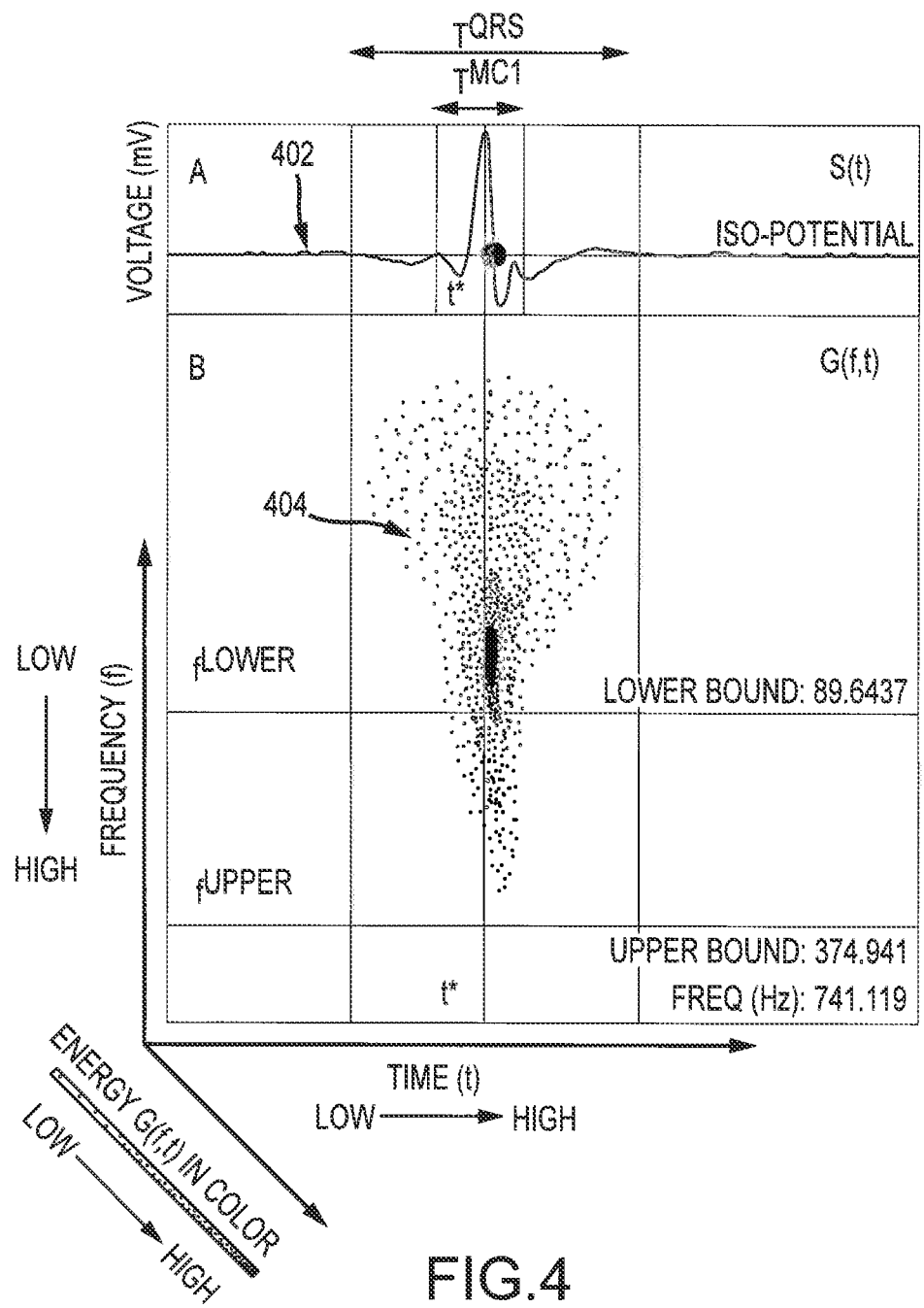
FIG. 4 depicts an electrogram from healthy tissue and the corresponding scalogram.

In block 304, the electrogram signal S(t) is transformed into the wavelet domain, which computes a scalogram G(f,t) (illustrated as scalogram 404 in panel B of FIG. 4). More specifically, G(f,t) can be computed for a preset window, referred to herein as a "Roving Activation Interval" ("RAI") about a reference time point, referred to herein as $T_{ref}$. According to aspects disclosed herein, $T_{ref}$ corresponds to QRS activity detected using a user-defined reference cardiac signal, such as the signal from an EKG lead or the signal from an in vivo reference electrode.

Likewise, the width of the RAI can be user-defined. According to aspects of the disclosure, the RAI is between about 100 ms and about 300 ms wide.

For purposes of illustration, the figures herein are displayed in the full width of an exemplary RAI centered about an exemplary $T_{ref}$.

In embodiments, block 304 applies a continuous wavelet transform to the electrogram signal S(t). The mother wavelet used in the wavelet transform can be a high time-resolution mother wavelet, such as a Paul wavelet, or a high frequency-resolution mother wavelet, such as a Morlet wavelet, both of which will be familiar to those of ordinary skill in the art. Of course, other mother wavelets can also be employed without departing from the scope of the instant teachings. The teachings herein can also be applied using discrete wavelet transforms.

If desired, noise can be removed from the scalogam G(f,t) in block 306. For example, the energy amplitudes within the RAI can be normalized to values between 0 and 1, with the highest energy amplitude within the RAI corresponding to 1. Once the energy amplitudes have been so normalized, values of G(f,t) less than a preset, and optionally user-defined, noise threshold, such as about 0.2, can be set to zero, and thus eliminated from the scalogam G(f,t).

In block 308, at least one energy function L(t) is computed of the scalogram G(f,t). The at least one energy function can be of form $L(t)=\Sigma G(f,t)$.

Figure 5A:
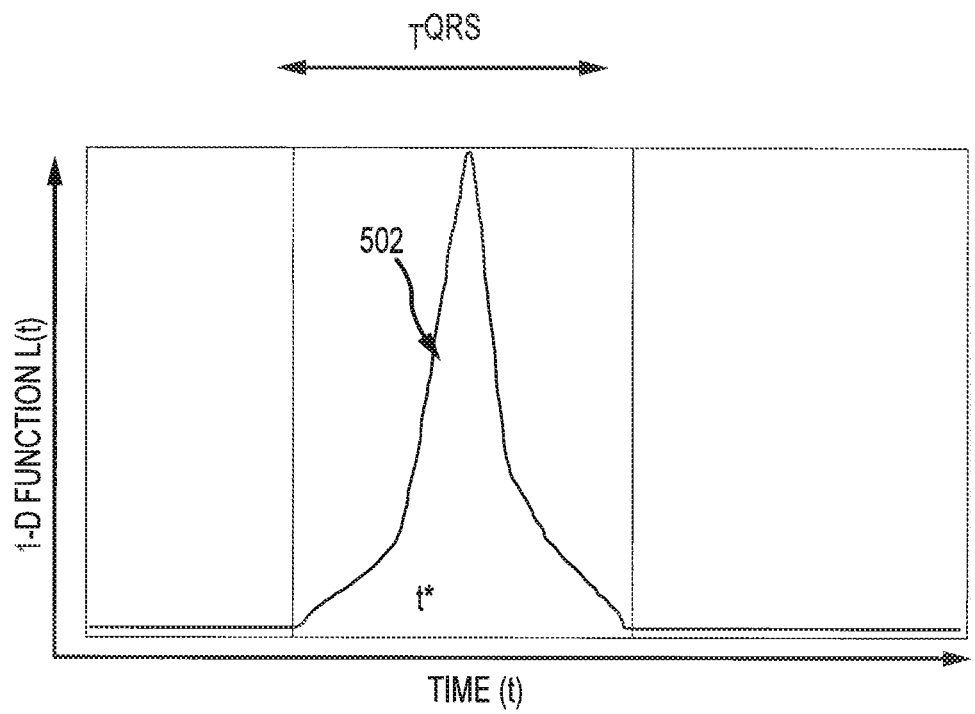
FIG. 5A depicts an energy function of the scalogram of FIG. 4.

In some embodiments of the disclosure, f ranges from about 0 Hz to about 1000 Hz. This frequency range will capture typical cardiac QRS activity. FIG. 5A depicts an energy function 502 of scalogam 404 in FIG. 4 where f ranges from about 0 Hz to about 1000 Hz.

Figure 5B:
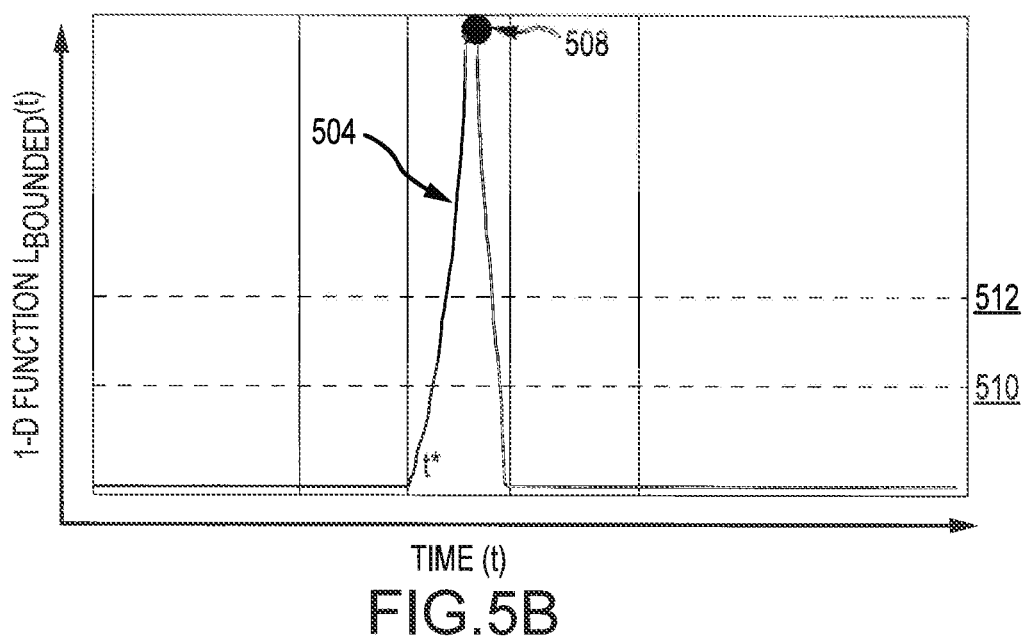
FIG. 5B depicts a bounded energy function of the scalogram of FIG. 4.

In other embodiments of the disclosure, f covers a cardiac activity frequency range between a preset lower frequency limit and a preset upper frequency limit. These embodiments are referred to herein as "bounded energy function" embodiments, and are advantageous in the context of capturing and decoupling near-field and far-field components of the electrogram signal S(t). One exemplary bounded energy function has a preset lower frequency limit of about 100 Hz and a preset upper frequency limit of about 700 Hz; FIG. 5B depicts such a bounded energy function 504 of scalogram 404 in FIG. 4.

In still other embodiments of the disclosure, the at least one energy function L(t) is an energy frequency function. The energy frequency function can be of form $L^{Freq}(t)=f$, where f is the highest frequency, between about 0 Hz and about 1000 Hz, at which the scalogram G(f,t) exceeds a preset (e.g., user-defined) peak threshold (e.g., about 90 Hz for a near-field peak threshold and about 70 Hz for a far-field peak threshold).

In block 310, at least one metric of the electrogram signal S(t) is computed in the wavelet domain using the energy function(s) L(t). Several metrics are described in further detail below.

Cardiac Activity Duration. A first metric that can be computed in the wavelet domain using the energy function(s) L(t) is the cardiac activity duration, denoted $T^{QRS}$ throughout the Figures. To compute the cardiac activity duration, the energy function L(t) can be converted to a pulse wave $L^{Pulse}(t)$, where $$L^{Pulse}(t) = \begin{cases} 1, \text{ if } L(t) > 0 \\ 0, \text{ otherwise} \end{cases}.$$

can then be defined as the duration of the pulse wave $L^{Pulse}(t)$.

Duration of Near- and Far-Field Components. A second metric that can be computed in the wavelet domain using the energy fiinction(s) L(t), and in particular a bounded energy function L(t), is the duration of multiple near- and far-field components. An initial step in computing this metric is to detect near-field and far-field activity peaks in the energy function L(t).

Figure 8:
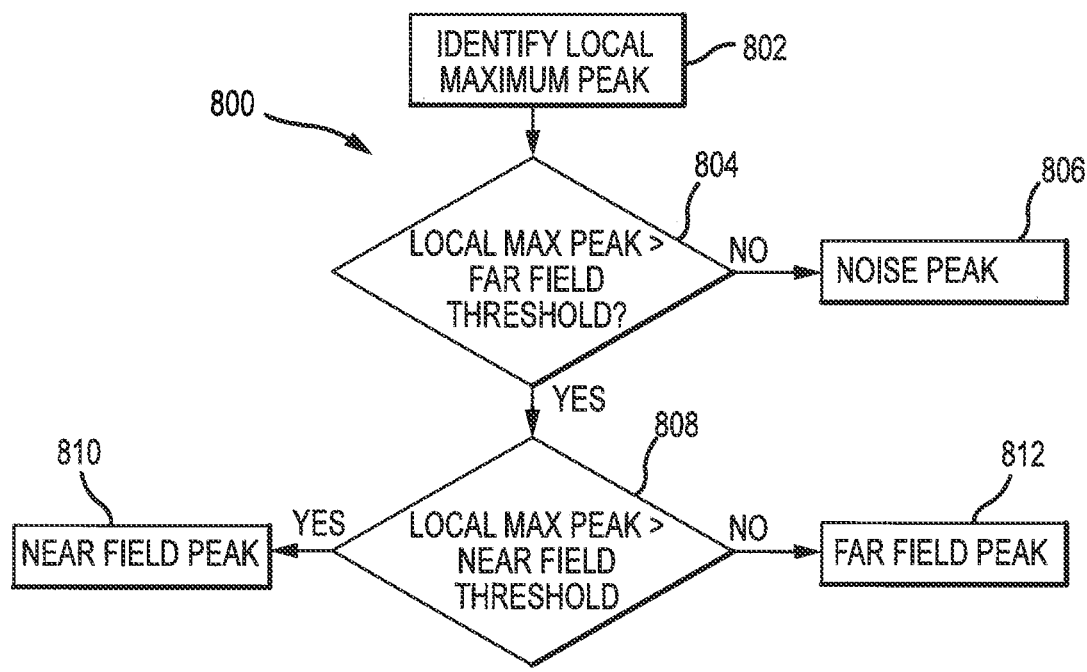
FIG. 8 is a flowchart of representative steps that can be followed to identify and categorize peaks in an energy function.

Thus, for example, a plurality of local maximum peaks can be detected in the energy function L(t), and each local maximum peak can be categorized as a near-field peak, a far-field peak, or a noise peak, according to the following logic, which is depicted in flowchart 800 in FIG. 8:

In block 802, a. local maximum peak can be identified;
In block 804, L(t) at the peak can be compared to a far field threshold; if it does not exceed the far field threshold, then the peak can be categorized as a noise peak and discarded (block 806);
In block 806, L(t) at the peak can be compared to a near field threshold; if it exceeds the near field threshold, then the peak can be categorized as a near field peak (block 810);
Otherwise, the peak can be categorized as a far field peak (block 812).

In some embodiments, the preset far field threshold is about 2.5 times the length of the electrogram signal S(t) and the preset near field threshold is about 5 times the length of the electrogram signal S(t).

Referring again to bounded energy function 504 in FIG. 5B, peak 508 exceeds both the far field threshold 510 and the near field threshold 512, and therefore would be categorized as a near-field peak.

Similar logic can be used to categorize peaks within the energy frequency function $L^{Freq}(t)$ described above as far field, near field, or noise, for example using the peak thresholds discussed above.

Once the peaks are categorized, it is possible to compute a near-field component duration and/or a far-field component duration for the electrogram signal S(t). The energy function (e.g., bounded energy function 502 in FIG. 5B) can be converted to a pulse wave $L^{Pulse}(t)$ having one or more pulses, where $$L^{Pulse}(t) = \begin{cases} 1, \text{ if } L(t) > 0 \\ 0, \text{ otherwise} \end{cases}.$$

The number of pulses in $L^{Pulse}(t)$ is dependent upon the morphology of the electrogram signal S(t). If electrogram signal S(t) is from healthy tissue with a single sharp QRS activity, such as signal 402 in FIG. 4, $L^{Pulse}(t)$ will have a single pulse.

Figure 6A:
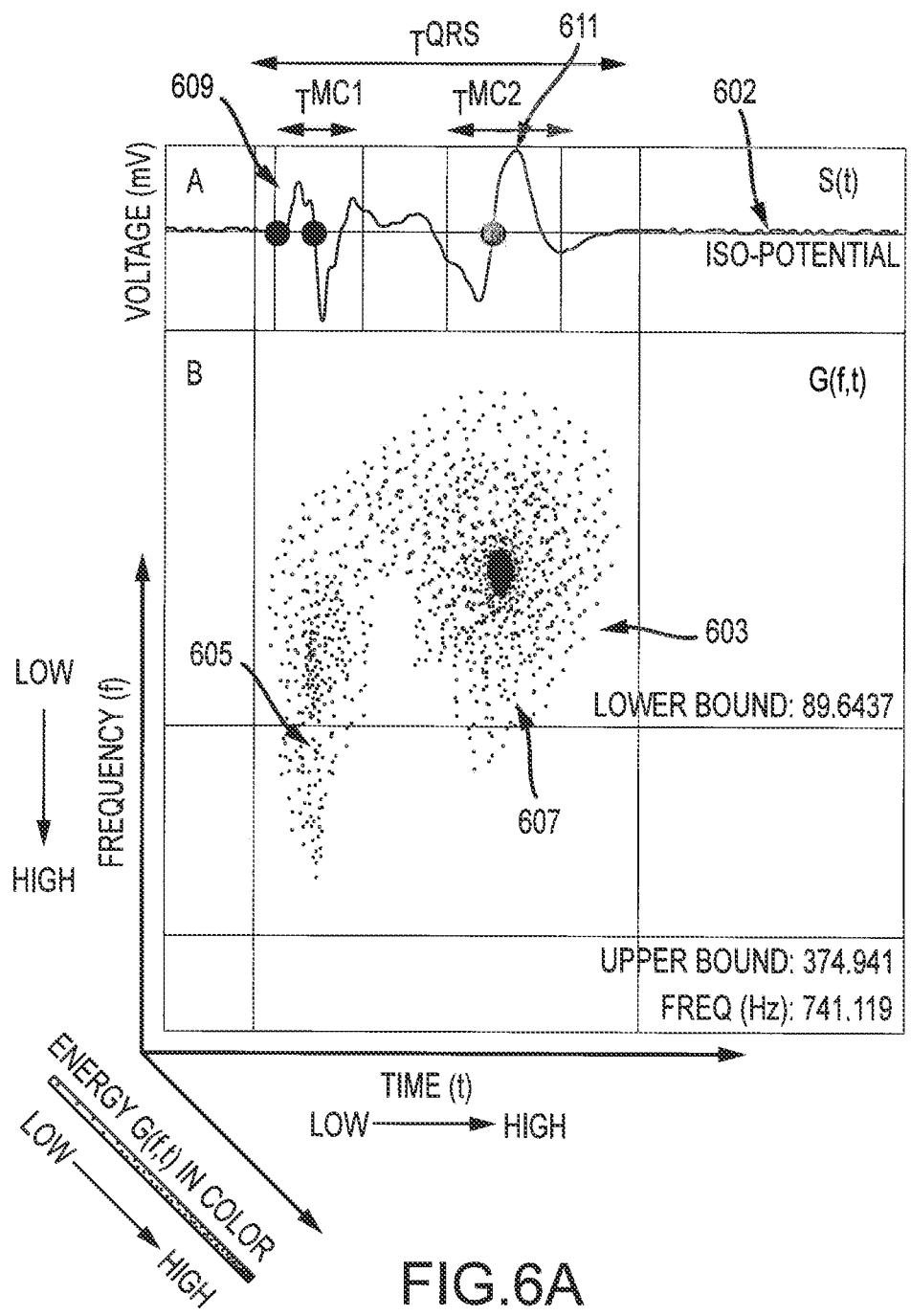
FIG. 6A depicts an electrogram having morphology Form 1 and the corresponding scalogram.
Figure 6B:
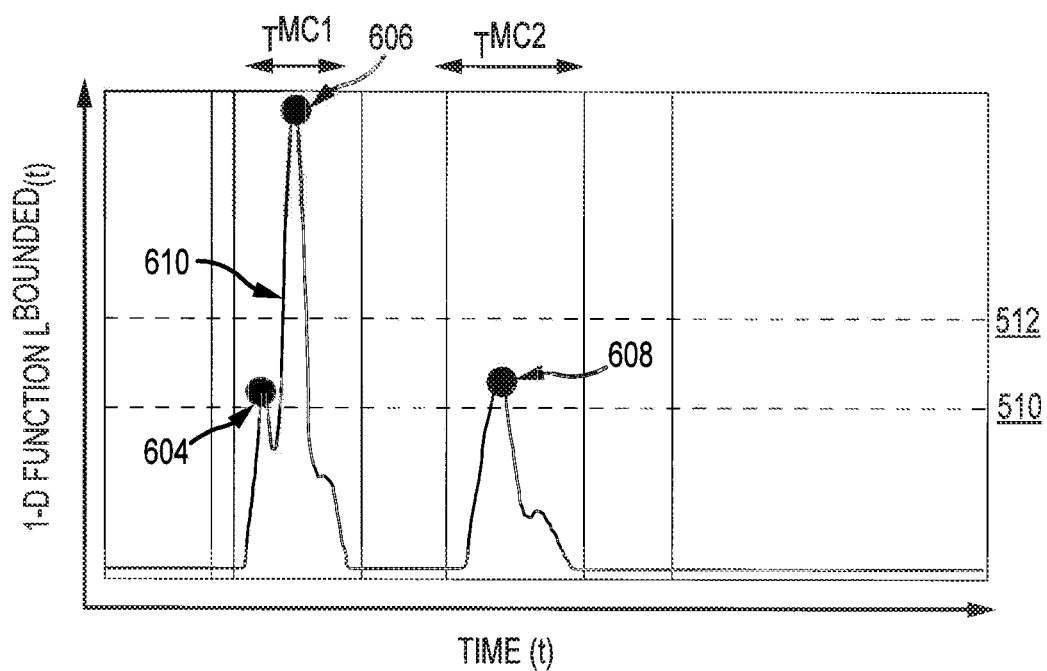
FIG. 6B depicts a bounded energy function of the scalogram of FIG. 6A.

If the electrogram signal S(t) is of Form 1 described above, such as signal 602 in panel A of FIG. 6A, $L^{Pulse}(t)$ will have multiple pulses, which result from the multiple peaks 604 (far-field peak), 606 (near-field peak), 608 (far-field peak) shown in bounded energy function 610 in FIG. 6B.

Figure 7A:
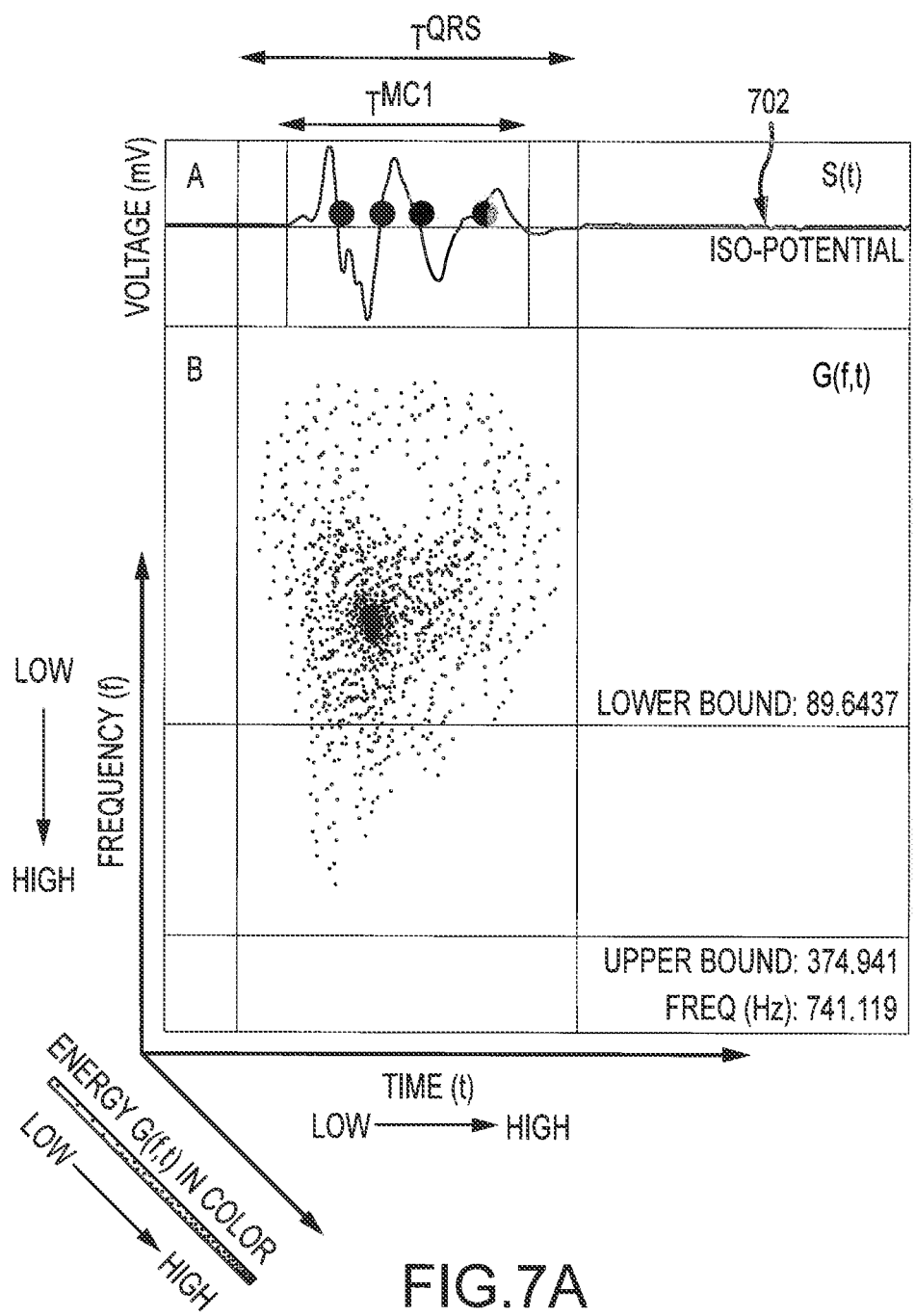
FIG. 7A depicts an electrogram having morphology Form 2 and the corresponding scalogram.

If the electrogram signal S(t) is of Form 2 described above, such as signal 702 in panel A of FIG. 7A, $L^{Pulse}(t)$ will again have only a single pulse, because the peaks 704 (near-field peak), 706 (near-field peak), 708 (far-field peak), and 710 (noise peak) of bounded energy function 712 (see FIG. 7B) will be fused together.

If a pulse in $L^{Pulse}(t)$ includes a near-field peak (e.g., peak 508 in FIG. 5B; peak 606 in FIG. 6B; peaks 704 and 706 in FIG. 7B), then the near-field component duration for the electrogam signal S(t) can be defined to be equal to the duration of the pulse. This is denoted throughout the Figures as $T^{MC1}$.

If, on the other hand, a pulse in $L^{Pulse}(t)$ includes a fear-field peak but not a near-field peak (e.g., peak 608 in FIG. 6B), then the far-field component duration for the electrogram signal S(t) can be defined to be equal to the duration of the pulse. This is denoted in FIGS. 6A and 6B as $T^{MC2}$.

Number of Multiple Components. A third metric that can be computed in the wavelet domain using the energy function(s) L(t) is the number of components present in the electrogram signal S(t). A plurality of local maximum peaks can be detected in the energy function L(t), and each local maximum peak can be categorized as a near-field peak, a far-field peak, or a noise peak, as described above. The total number of near-field and far-field peaks in the energy function L(t) (that is, the total number of local maximum peaks excluding noise peaks) can be defined to be the number of multiple components for the electrogram signal S(t).

Figure 7B:
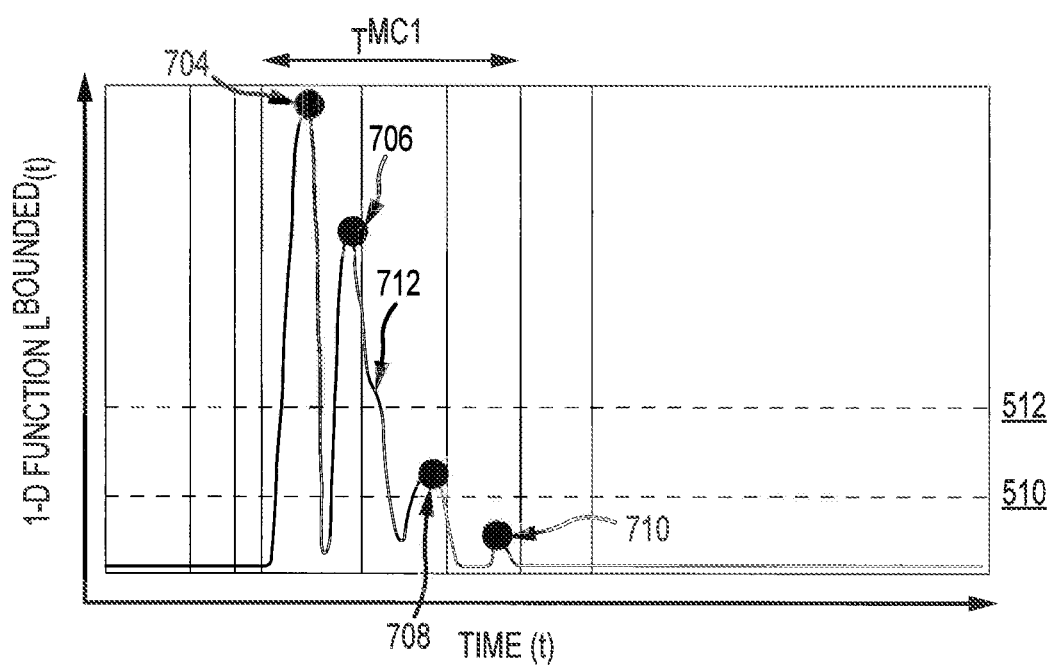
FIG. 7B depicts a bounded energy function of the scalogram of FIG. 7A.

Slope of the Sharpest Component. A fourth metric that can be computed in the wavelet domain using the energy function(s) L(t) is the slope of the sharpest component of the electrogram signal S(t). This can be computed by first identifying the maximum energy near-field peak of the plurality of local maximum peaks in the energy function L(t). With reference to FIGS. 5B, 6B, and 7B, the maximum energy near-field peaks are peaks 508, 606, and 704, respectively.

Once the maximum energy near-field peak has been identified, S(t) can be examined within a preset refractory window about the peak to determine the maximum slope thereof. More particularly, a maximum value of the first derivative S'(t) of the electrogram signal S(t) can be computed within the refractory window, and this maximum value of S'(t) can be defined as the slope of the sharpest component of S(t). In embodiments of the disclosure, the refractory window extends about 5 ms to either side of the peak (e.g., the refractory window is about 10 ms wide, centered on the peak).

Scalogram Width. The slope of the sharpest component of the electrogram signal S(t) can also be inferred from the width of the scalogram G(f,t). The narrower the width of a peak in the scalogram G(f,t) corresponding to a peak in the electrogram signal S(t), the sharper the slope of the electrogram signal S(t) about that peak.

For example, referring to peaks 609, 611 in electrogram signal 602 in panel A of FIG. 6A, the width of the scalogram 603 in panel B has two corresponding peaks 605, 607. Because the width of peak 605 is narrower than that of peak 607, the slope of electrogram signal 602 is sharper about peak 609 than it is about peak 611. This relationship is also visible in FIG. 6B in the relative widths of the pulse durations $T^{MC1}$ and $T^{MC2}$ about peaks 606 and 608, respectively.

Energy Ratio. Yet another metric that can be computed in the wavelet domain using the energy function(s) L(t) is an energy ratio. According to embodiments of the disclosure, two energy functions are computed: A high frequency energy function $L^{High}(t)=\Sigma G(f^{high},t)$ and a low frequency energy function $L^{Low}(t)=\Sigma G(f^{Low},t)$. In aspects of the disclosure, $f^{Low}$ can be between about 10 Hz and about 60 Hz and 60 Hz and $f^{High}$ can be between about 60 Hz and about 300 Hz, but other ranges (e.g., about 10 Hz to about 50 Hz for $f^{Low}$ and about 50 Hz to about 300 Hz for $f^{High}$ or about 10 Hz to about 100 Hz for $f^{Low}$ and about 100 Hz to about 300 Hz for $f^{High}$) are contemplated.

Once the energy functions are computed, the ratio of $L^{High}(t)$ to $L^{Low}(t)$ can be computed.

Cycle Length-based Metrics. Still further metrics that can be computed in the wavelet domain using the energy function(s) L(t) are cycle length-based metrics, such as mean cycle length and/or cycle length variation/standard deviation. These cycle length-based metrics can also be computed using the ratio of $L^{High}(t)$ to $L^{Low}(t)$ described above. In particular, the ratio of $L^{High}(t)$ to $L^{Low}(t)$ can be used to detect local activation times in the electrogram signal S(t) when the ratio of $L^{High}(t)$ to $L^{Low}(t)$ exceeds a preset detection threshold. In embodiments, the preset detection threshold is about 0.5. The ordinarily skilled artisan will be familiar with the computation of mean cycle lengths and cycle length variances/standard deviations from a plurality of local activation times.

Figure 3:
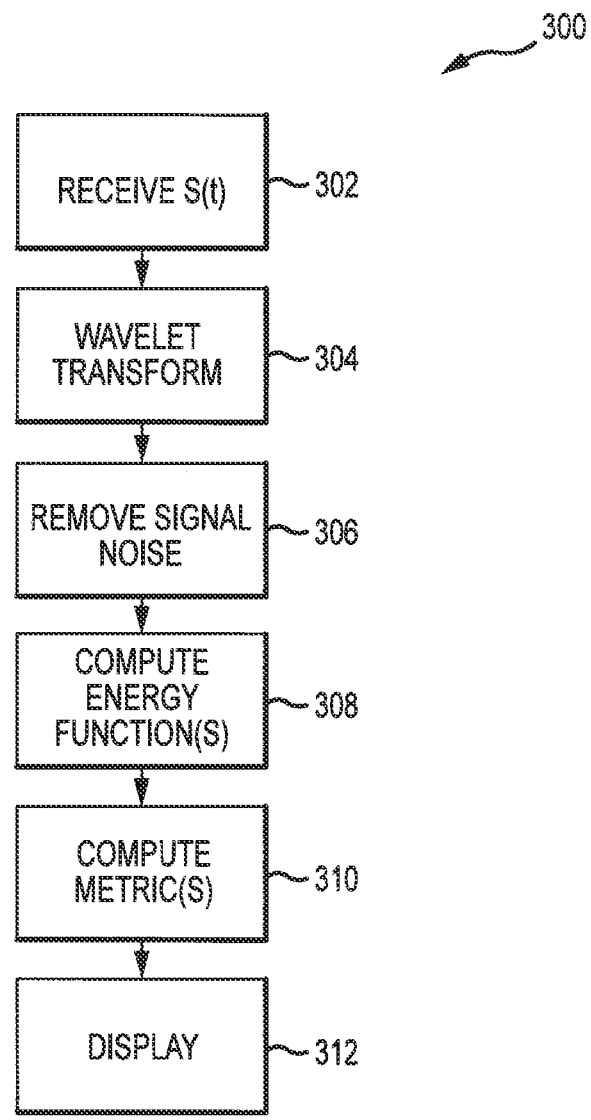
FIG. 3 is a flowchart of representative steps that can be followed to map cardiac activity.

Returning once more to flowchart 300 in FIG. 3, once the metric(s) have been computed, they can be displayed in block 312, for example as an electrophysiology map on a cardiac model output on display 23 of computer system 20 depicted in FIG. 1. As described above, various techniques familiar in the art can be used to generate a graphical representation from a plurality of electrophysiology data points, including the metrics described herein, such that a detailed discussion of the creation of an electrophysiology map is not necessary to an understanding of the present disclosure.

Although several embodiments of this invention have been described above with a certain degree of particularity, those skilled in the art could make numerous alterations to the disclosed embodiments without departing from the spirit or scope of this invention.

For example, the teachings herein can be applied not only to intracardiac electrogram signals, but also to surface ECG signals.

As another example, the teachings herein can be used to compute an electrogram fractionation measure from sinus rhythm electrogram signals, paced electrogram signals, and arrhythmic electrogram signals (e.g., atrial or ventricular tachycardia; atrial fibrillation).

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention, Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of mapping cardiac activity, comprising:
receiving an electrogram signal S(t) at an electroanatomical mapping system; and
executing, via the electroanatomical mapping system, a process comprising:
transforming the electrogram signal S(t) into the wavelet domain, thereby computing a scalogram G(f, t);
computing at least one energy function L(t) of the scalogram G(f, t), wherein L(t)=$\Sigma$G(f,t); and
computing at least one metric of the electrogram signal S(t) using the at least one energy function L(t) by computing a pulse wave $L^{Pulse}(t)$ having a pulse duration and one or more pulses, where $$L^{Pulse}(t) = \begin{cases} 1, \text{ if } L(t) > 0 \\ 0, \text{ otherwise} \end{cases};$$

and
displaying a graphical representation of the at least one metric of the electrogram signal S(t) on a graphical representation of a cardiac model.

2. The method according to claim 1, wherein transforming the electrogram signal S(t) into the wavelet domain comprises applying a continuous wavelet transformation to the electrogram signal S(t) to compute the scalogram G(f, t).

3. The method according to claim 1, further comprising setting values of G(f, t) less than a preset noise threshold to zero.

4. The method according to claim 1, wherein the at least one metric of the electrogram signal S(t) comprises a QRS activity duration for the electrogram signal S(t), wherein the QRS activity duration for the electrogram signal S(t) is defined to be equal to the pulse duration of the pulse wave $L^{Pulse}(t)$.

5. The method according to claim 1, wherein f is within a cardiac activity frequency range defined by a preset lower frequency limit and a preset upper frequency limit.

6. The method according to claim 5, further comprising:
detecting a plurality of local maximum peaks in the at least one energy function L(t); and
categorizing each local maximum peak of the plurality of local maximum peaks as a near-field peak, a far-field peak, or a noise peak.

7. The method according to claim 6, wherein categorizing each local maximum peak of the plurality of local maximum peaks as a near-field peak, a far-field peak, or a noise peak comprises:
categorizing a local maximum peak as a near-field peak if the at least one energy function L(t) exceeds a preset near field threshold at the local maximum peak;
categorizing the local maximum peak as a far-field peak if the at least one energy function L(t) exceeds a preset far field threshold and not the preset near field threshold at the local maximum peak; and categorizing the local maximum peak as a noise peak otherwise.

8. The method according to claim 6, wherein the at least one metric of the electrogram signal S(t) comprises at least one of a near-field component duration and a far-field component duration for the electrogram signal S(t), computed by a method comprising:

for each pulse of the one or more pulses of the pulse wave $L^{Pulse}(t)$:

if the pulse includes a near-field peak, defining the near-field component duration for the electrogram signal S(t) to be equal to a duration of the pulse; and if the pulse includes a far-field peak, defining the far-field component duration for the electrogram signal S(t) to be equal to the duration of the pulse.

9. The method according to claim 6, wherein the at least one metric of the electrogram signal S(t) comprises a number of multiple components for the electrogram signal S(t), wherein the number of multiple components for the electrogram signal S(t) is defined to be equal to a total number of the plurality of local maximum peaks in the at least one energy function L(t).

10. The method according to claim 6, wherein the at least one metric of the electrogram signal S(t) comprises a slope of a sharpest component of the electrogram signal S(t).

11. The method according to claim 10, wherein the slope of a sharpest component of the electrogram signal S(t) is computed by a method comprising:

identifying a maximum energy near-field peak of the plurality of local maximum peaks in the at least one energy function L(t);

computing a maximum value of a first derivative S'(t) of the electrogram signal S(t) within a preset refractory window surrounding the maximum energy near-field peak; and defining the maximum value of the first derivative S'(t) of the electrogram signal S(t) within the preset refractory window as the slope of the sharpest component of the electrogram signal S(t).

12. The method according to claim 1, wherein:

the at least one energy function L(t) comprises:

computing a high frequency energy function $L^{High}(t) = \Sigma G(f^{High}, t)$; and computing a low frequency energy function $L^{Low}(t) \Sigma G(f^{Low}, t)$; and computing the at least one metric of the electrogram signal S(t) comprises computing a ratio of $L^{High}(t)$ to $L^{Low}(t)$.

13. The method according to claim 12, wherein $f^{High}$ is between 60 Hz and 300 Hz and $f^{Low}$ is between 10 Hz and 60 Hz.

14. The method according to claim 12, wherein the at least one metric of the electrogram signal S(t) comprises a cycle-length based metric computed using the ratio of $L^{High}(t)$ to $L^{Low}(t)$.

15. The method according to claim 14, wherein the cycle-length based metric is computed using the ratio of $L^{High}(t)$ to $L^{Low}(t)$ based upon a plurality of local activation times detected when the ratio of $L^{High}(t)$ to $L^{Low}(t)$ exceeds a preset threshold.

16. A system for mapping cardiac activity, comprising:

a wavelet transformation processor configured:

to receive an electrogram S(t);

to transform the electrogram signal S(t) into the wavelet domain, thereby computing a scalogram G(f, t); and to compute at least one energy function L(t) of the scalogram G(f, t), wherein $L(t) = \Sigma G(f, t)$; and a mapping processor configured to:

compute at least one metric of the electrogram signal S(t) in the wavelet domain using the at least one energy function L(t), comprising computing a pulse wave $L^{Pulse}(t)$ having a pulse duration and one or more pulses, where $$L^{Pulse}(t) = \begin{cases} 1, & \text{if } L(t) > 0 \\ 0, & \text{otherwise} \end{cases};$$

and output a graphical representation of the at least one metric of the electrogram signal S(t) on a graphical representation of a cardiac model; and a display to display the graphical representation.

17. The system according to claim 16, wherein the at least one metric of the electrogram signal S(t) is selected from the group consisting of: a QRS activity duration for the electrogram signal S(t); a near-field component duration for the electrogram signal S(t); a far-field component duration for the electrogram signal S(t); a number of multiple components for the electrogram signal S(t); a slope of a sharpest component of the electrogram signal S(t); a scalogram width; an energy ratio in the electrogram signal S(t); and a cycle-length based metric of the electrogram signal S(t).

* * * * *